US00PP09320P

United States Patent [19]

Small et al.

[11] Patent Number: Plant 9,320

[45] Date of Patent: Oct. 10, 1995

[54] STRAWBERRY PLANT NAMED 'CATALINA'

[76] Inventors: David Small, 401 Las Vegas St., Morro Bay, Calif. 93442; Jim Bagdasarian, 3720 Tiffani Ct., Santa Cruz, Calif. 95065

[21] Appl. No.: 294,729

[22] Filed: Aug. 23, 1994

[51] Int. Cl.[6] ..... A01H 5/00

[52] U.S. Cl. ..... Plt./49

[58] Field of Search ..... Plt./49, 48

[56] References Cited

U.S. PATENT DOCUMENTS

| | | | |
|---|---|---|---|
| P.P. 5,262 | 7/1984 | Voth et al. | Plt./48 |
| P.P. 5,266 | 7/1984 | Bringhurst et al. | Plt./49 |
| P.P. 6,578 | 1/1989 | Voth et al. | Plt./48 |
| P.P. 7,024 | 9/1989 | Johnson, Jr. et al. | Plt./49 |
| P.P. 7,614 | 8/1991 | Bringhurst et al. | Plt./49 |
| P.P. 7,615 | 8/1991 | Bringhurst et al. | Plt./49 |
| P.P. 8,086 | 1/1993 | Nelson et al. | Plt./49 |
| P.P. 8,708 | 5/1994 | Voth et al. | Plt./49 |

*Primary Examiner*—James R. Feyrer

*Attorney, Agent, or Firm*—David A. Farah; Sheldon & Mak, Inc.

[57] ABSTRACT

A new and distinct cultivar of strawberry named 'Catalina' is described. 'Catalina' is a short day cultivar with a tendency to be everbearing in more northern regions. Catalina produces a significant amount of fruit in a short period without the substantial periodic decreases characteristic of existing commercial cultivars. Additionally, 'Catalina' produces abudant primary, secondary and tertiary flowers which in turn produce a high yield of well shaped, unblemished fruit as compared to commercial varieties. 'Catalina' is further superior to existing cultivars in that it is adapted to grow in the soils and under the climatic conditions of all commercial strawberry growing regions in California.

5 Drawing Sheets

DESCRIPTION

The invention relates to a new and distinctive short-day type strawberry cultivar, designated 'Catalina,' having an everbearing tendency. Catalina is the result of a cross of A41×Seascape (U.S. Plant Pat. No. 7,614) made in 1991.

'Catalina' was first selected as a seedling variety at the New West Fruit Corporation, Oxnard, Calif. breeding test plot in 1993 where it was designated as 19B50. It was tested later as advanced selection B10.

'Catalina' has been propagated asexually by runners and has been tested at New West Fruit Corp. test plots throughout the various fruiting areas of California.

'Catalina' is earlier fruiting than 'Chandler,' 'Camarosa,' or 'Selva'. It has a much earlier and stronger fruit production with larger and more consistent fruit size that is superior to 'Chandler,' 'Camarosa,' 'Selva,' or 'Seascape.' It has the unique ability to produce equally well in all curently planted commercial strawberry growing areas. As a short-day variety, it has the ability to produce a significant amount of fruit in a short period of time, without the substantial peaks and valleys that exist with commonly grown commerical varieties. It tends to produce fruit much more evenly throughout the season, without the radical size-reduction characteristicly seen in late season production of currently available strawberry cultivars. Further, 'Catalina' produces a much higher number of well shaped, unblemished fruit than existing cultivars. A general comparison of the variety with 'Seascape' and 'Chandler' is given in Table 1.

IN THE DRAWINGS

VEGETATIVE CHARACTERISTICS

Figure 1:
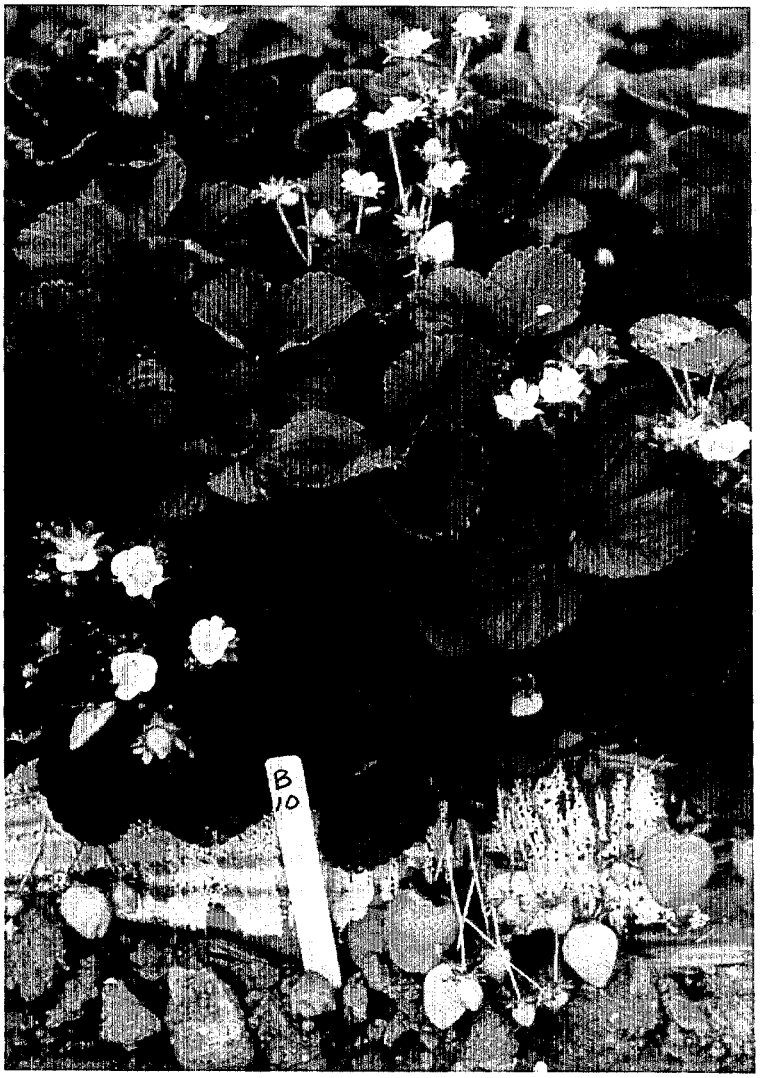
FIG. 1 shows typical growth, flowering and fruiting characteristics of the strawberry plant of the invention.

'Catalina' plants are semi-erect in growth habit, are more vigorous than 'Chandler,' 'Oso Grande,' 'Camarosa,' or 'Selva.' Catalina plants remain much more open throughout the season than currently grown varieties. Leaflets are orbicular and dentate, with a highly waxy cuticle.

Unline existing cultivars, which display significant chlorosis throughout much of the year, the leaves of 'Catalina' plants present a very strong and healthy appearance throughout the growing season, with new leaves being strongly emergent above the existing growth of the plant. Leaf color is similar to that seen in 'Seascape.' It is darker than 'Chandler, lighter than in 'Camarosa' and 'Selva,' and remains consistent in intensity throughout the growing season.

DISEASE AND PEST RESISTANCE

Catalina shows mild susceptibility to Powdery Mildew (*Sphagudtheia maculatus* spp. *fragariae*) and Angular Leaf Spot *Xanthomonas fragariae*). Catalina shows very good tolerance to Verticillium Wilt (Verticillium Algo-Atrum) and Phytophthora spp. Furthermore, Catalina shows good vigor in non-fumigated conditons.

FLOWERING AND FRUITING CHARACTERISTICS

The fruit of 'Catalina' is initially borne on single stems with separation of primary, secondary, and tertiary fruit taking place in the crown of the plant. As the season progresses the separation of the various stages of fruit place outside the crown creating a multiple inflorescence. 'Catalina' produces multicipital inflorescences with several racemes or cymes per peduncle, with no apparent loss of overall size or shape due to the amount of fruit borne on each peduncle. Inflorescences are very long and erect, standing above the plant, and drop quickly due to the weight of the fruit as it matures. 'Catalina' is self-fertile, and produces more than sufficient pollen throughout the season to insure very few malformed fruit.

'Catalina' fruit is medium- to long-conic to wide-shouldered wedge-shaped, and smooth, with the occasional creased or cockscombed primary. Fruit size is very good throughout the season, with little loss of size at the various stages of development on the inflorescence; very good size is actually regained, throughout the growing season, with each new inflorescence. The fruit is generally better shaped than the fruit of 'Chandler,' 'Oso Grande,' 'Camarosa,' 'Selva,' or 'Seascape.' Internally, the fruit is solid with the occasional primary fruit with having a slight cavity. Fruit color is a fine red color, slightly darker than 'Chandler', but not as dark as 'Oso Grande' or 'Seascape,' with good color saturation of the flesh. The interior color matches the exterior color. The achenes range from bright yellow to light red and are positioned even with the skin, which is very firm. The calyx is medium in size and tends to clasp the fruit, through it will occasionally reflex. The fruit is firm and very durable. 'Catalina' has a very glossy finish and is very appealing.

'Catalina' has soluble solid readings similar to 'Chandler'. The flavor of 'Catalina' is excellent, and is comparable to the best flavored cultivars now grown in California. The fruiting habit and many fruit qualities of 'Catalina' make it very suitable as both a fresh market and processing variety.

PRODUCTION CHARACTERISTICS

Production is superior to known strawberry cuultivars, both in volume and quality. Catalina plants are very vigorous, producing large, compound inflorescences with well developed primary, secondary and even tertiary fruit. Very good inflorescence size is actually regained, throughout the season, as new inflorescences are produced. Fruit quality is also excellent, with virtually all fruit produced showing enhanced shape and size, with very little blemishing. Thus, a very high percentage of fruit produced each is season can be sold.

Volume and quality of fruit is further enhanced by the strong vegetative vigor displayed by Catalina. The plants remain fresh green throughout the growing season, unlike most commercial cultivars that become tattered and chlorotic in mid and late season. Catalina is successful in both fumigated and non-fumigated fields and greenhouses. Further adding to the superiority of the hybrid is the fact that the plant can be grown successfully throughout all strawberry growing regions of California.

TABLE 1

MORPHOLOGICAL COMPARISON OF 'Catalina' TO RELATED VARIETIES

| | CATALINA | CHANDLER | SEA SCAPE |
|---|---|---|---|
| VEGETATIVE CHARACTERISTICS | | | |
| Leaf color: | medium green | light green | medium green |
| Leaf size: | large | medium | small |
| Cuticle: | waxy, shiny | dull | dull |
| Habit: | very open plant, with flat, upward cupping leaves; very vigorous in growth | dense plant, with upward cupping leaves | fairly open plant, with flat, upward cupping leaves; vigorous in growth |
| Chilling | very low chilling | very low | very high |
| Plant appearance: | maintains fresh, healthy appearance throughout growing season | poor plant appearance mid to late season | poor plant appearance mid to late season |
| FLOWERING/FRUITING CHARACTERISTICS | | | |
| Inflorescence: | highly branched with numerous secondary and tertiary flowers and fruits | not highly branched limited in production of secondary flowers and fruits | not highly branched, limited in production of secondary flowers and fruits |
| Fruit shape: | medium-conic, with little malformation in late season fruit; medium calyx | medium-to long-conic, with significant malformation in late season fruit; small to medium calyx | medium-to long-conic, with significant malformation in late season fruit; small-medium calyx |
| Fruit color: | dark red with good saturation in flesh | medium red flesh with only partial fruit saturation | medium to dark red, flesh not well saturated |
| Flesh character: | good firmness | good firmness | fair firmness |
| Seed: | seeds even with fruit surface | seeds raised as compared to fruit surface | Seeds even with fruit surface |
| Fruit set: | strong early, short day | strong early, very peaked | fair, building to fall |

We claim:

1. The new and distinct variety of strawbery plant described and illustrated and having the characteristics enumerated above.

* * * * *

UNITED STATES PATENT AND TRADEMARK OFFICE

CERTIFICATE OF CORRECTION

PATENT NO. : PP09320

DATED : October 10, 1995

INVENTOR(S) : David Small, et al

It is certified that error appears in the above-identified patent and that said Letters Patent is hereby corrected as shown below:

On the title page after item [76] insert the following:
--[73] Assignee: New West Fruit Corporation--

Signed and Sealed this

Sixteenth Day of July, 1996

*Attest:*

Bruce Lehman

BRUCE LEHMAN

*Attesting Officer*

*Commissioner of Patents and Trademarks*

UNITED STATES PATENT AND TRADEMARK OFFICE

CERTIFICATE OF CORRECTION

PATENT NO. : Plant 9,320

DATED : October 10, 1995

INVENTOR(S) : Small, et al

It is certified that error appears in the above-indentified patent and that said Letters Patent is hereby corrected as shown below:

The title page should be deleted and substitute therefor the attached title page.

Delete columns 3-6, and substitute therefor with the attched pages, consisting of columns 3-6.

Signed and Sealed this

Fifteenth Day of October, 1996

Bruce Lehman

*Attest:*

BRUCE LEHMAN

*Attesting Officer*

*Commissioner of Patents and Trademarks*

United States Patent [19]

Small et al.

[11] Patent Number: Plant 9,320

[45] Date of Patent: Oct. 10, 1995

[54] STRAWBERRY PLANT NAMED 'CATALINA'

[76] Inventors: David Small, 401 Las Vegas St., Morro Bay, Calif. 93442; Jim Bagdasarian, 3720 Tiffani Ct., Santa Cruz, Calif. 95065

[21] Appl. No.: 294,729

[22] Filed: Aug. 23, 1994

[51] Int. Cl.[6] ..... A01H 5/00

[52] U.S. Cl. ..... Plt./49

[58] Field of Search ..... Plt. 49, 48

[56] References Cited

U.S. PATENT DOCUMENTS

| | | | |
|---|---|---|---|
| P.P. 5,262 | 7/1984 | Voth et al. | Plt./48 |
| P.P. 5,266 | 7/1984 | Bringhurst et al. | Plt./49 |
| P.P. 6,578 | 1/1989 | Voth et al. | Plt./48 |
| P.P. 7,024 | 9/1989 | Johnson, Jr. et al. | Plt./49 |
| P.P. 7,614 | 8/1991 | Bringhurst et al. | Plt./49 |
| P.P. 7,615 | 8/1991 | Bringhurst et al. | Plt./49 |
| P.P. 8,086 | 1/1993 | Nelson et al. | Plt./49 |
| P.P. 8,708 | 5/1994 | Voth et al. | Plt./49 |

*Primary Examiner*—James R. Feyrer

*Attorney, Agent, or Firm*—David A. Farah; Sheldon & Mak, Inc.

[57] ABSTRACT

'Catalina' is a short-day cultivar with an everbearing tendency. Its buds and fruit are always produced well away from the plant canopy. 'Catalina' produces a considerable amount of fruit in a short period without the substantial periodic decreases characteristic of existing commercial cultivars. Additionally, 'Catalina' produces abundant primary, secondary and tertiary flowers which in turn produce a high yield of well shaped, unblemished fruit. The 'Catalina' plant retains a strong, healthy appearance throughout the growing season and does not undergo chlorosis. 'Catalina' is further superior to existing cultivars in that it is adapted to grow in the soils and under the climatic conditions of all commercial strawberry growing regions in California.

5 Drawing Sheets

DESCRIPTION

This invention relates to a new and distinctive short-day type strawberry cultivar, designated 'Catalina', which resulted from a cross performed in 1991 between a New West Fruit Corporation proprietary plant designated A41 and the cultivar 'Seascape' (U.S. Plant Pat. No. 7,614). The proprietary plant A41, initially designated 39A15, resulted from open-pollination. A41 was maintained exclusively for the purposes of breeding, was not released to growers, and was selected as parent material purely as a source of genetic diversity. A41 displayed a slight everbearing tendency, and produced about 125,000 plants to acre reflecting a 9:1 increase. It had medium vigor and had a dark, dull leaf surface, darker than 'Catalina'. Its fruit was medium sized, short-conic and smooth, with a slightly orange exterior with whitish interior. Its seeds were extruded. A41 was susceptible to *Colletotrichum* sp., various *Phytophthora* diseases, *Xanthomonas* and *Mytophaerella fragariae*.

'Catalina' was first selected as a seedling variety at the New West Fruit Corporation, Oxnard, California breeding test plot in 1993 and has been propagated asexually by runners. It was originally designated 19B50 and later designated as advanced selection B10. Asexual propagules from this original source have been tested at New West Fruit Corporation test plots throughout the various fruiting areas of California.

Figure 2:
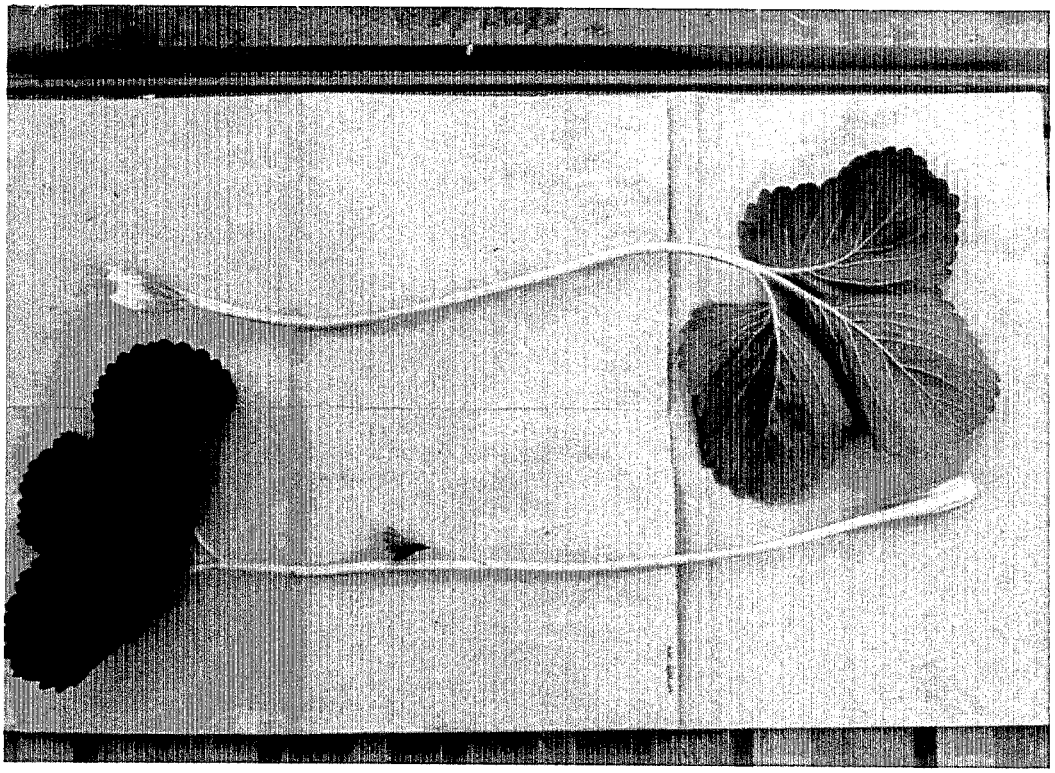
FIG. 2A shows a typical infructescense in early fruit.
FIG. 2B shows the abaxial and adaxial aspects of a typical mid-summer leaf.
Figure 3:
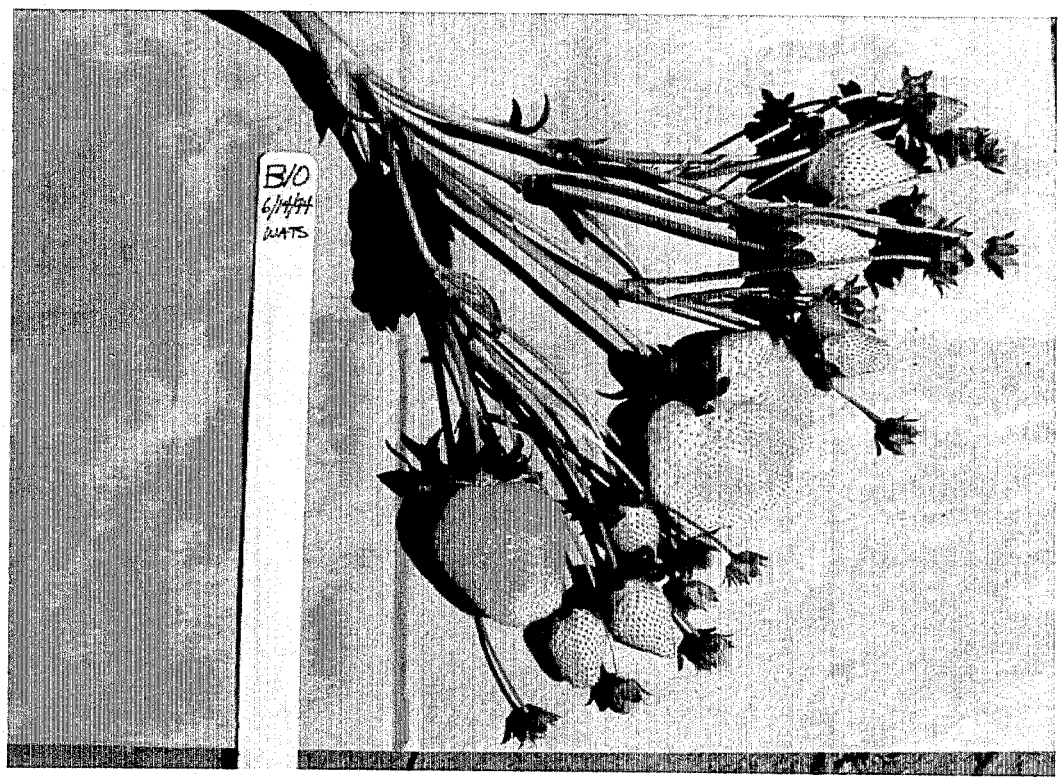
FIG. 3A shows representative whole fruit.
FIG. 3B shows representative fruit in cross and longitudinal section.
Figure 4:
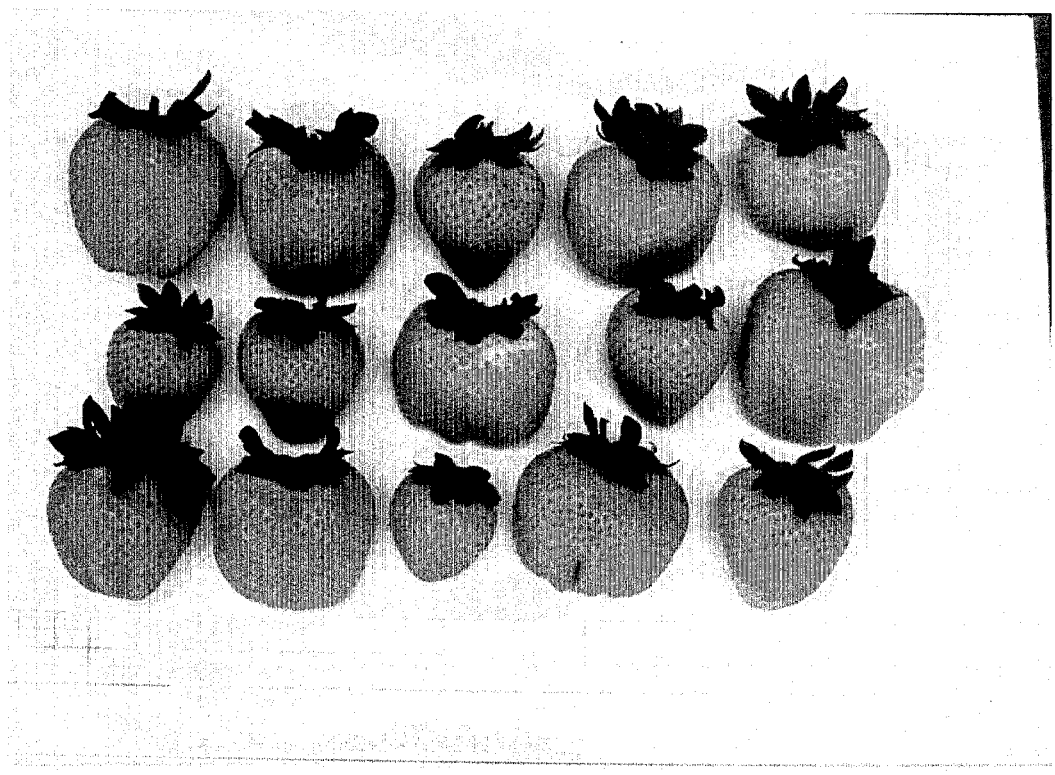

In the Figures:

FIG. 1 shows general flowering and fruiting characteristics of the 'Catalina' plant;

FIG. 2 shows abaxial (top) and adaxial (bottom) aspects of typical mature midsummer leaves;

FIG. 3 shows a typical infructescense in early fruit;

FIG. 4 shows representative whole fruit; and

Figure 5:
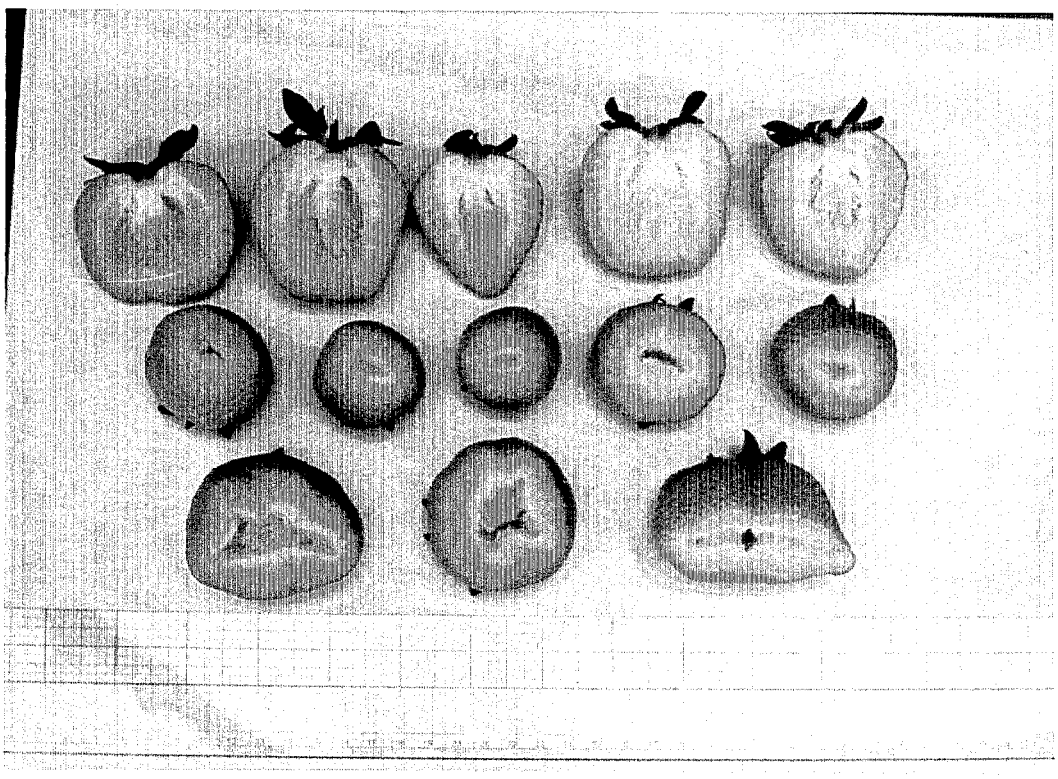

FIG. 5 shows representative fruit in longitudinal section and transverse sections.

PLANTS AND FOLIAGE

FIG. 1 shows a 'Catalina' plant demonstrating its general flowering and fruiting characteristics. As can be seen, fruiting plants of 'Catalina' grow semi-erect. Its flat to upward cupping leaves are generally similar to plants of 'Chandler' (U.S. Plant Pat. 5,262) and 'Seascape'. 'Catalina' plants, however, are more open than 'Seascape' and much more open than 'Chandler', and they remain open throughout the growing season unlike 'Chandler', 'Oso Grande', 'Selva' and 'Seascape'.

'Catalina' is particularly advantageous in that its buds and fruit are always produced well away from the plant canopy. This attribute renders 'Catalina' superior to currently grown cultivars such as 'Camarosa', 'Seascape' and 'Selva', because it allows for more efficient pollination, more even coloring of the fruit and easier hand harvesting. Further, having the buds and fruit outside the canopy increases their exposure to moving air, thereby reducing the incidence of diseases.

'Catalina' plants have mature stem lengths, that is the maximum dimension of the stem from the crown to the distal tip of the leaves, ranging from about 1 mm to 45 mm. Under reasonably favorable environmental conditions, the expected stem length is between about 18 mm and 35 mm. Thus, 'Catalina' plants are more vigorous than plants of 'Camarosa' (U.S. Plant Pat. 8,708), 'Chandler', 'Oso Grande' (U.S. Plant Pat. 6,578), or 'Selva' (U.S. Plant Pat. 5,266), and at least as vigorous as plants of 'Seascape.'

Referring to FIG. 2, there are illustrated abaxial (top) and adaxial (bottom) aspects of typical mature midsummer 'Catalina' plant leaves. As can be seen, 'Catalina' plant leaves are orbicular and dentate, similar to 'Seascape' leaves, with a shiny, highly waxy cuticle and about 18 to 24 serrations per leaf. The leaves of 'Catalina' plants appear strong and healthy throughout the growing season, with new leaves emerging above the existing plant growth.

'Catalina' plant leaves are medium green, similar to 'Seascape' plant leaves, darker than 'Chandler' plant leaves but lighter than either 'Camarosa' or 'Selva' plant leaves. Visual comparisons of 'Catalina' leaf color to 'Camarosa' and 'Chandler' leaf color were made according to the PANTONE® Color Formula Guide 1000 (Pantone, Inc. 590 Commerce Boulevard, Carlstadt, NJ USA 07072-3098). The results are given in Table 1 below. Unlike existing cultivars such as 'Camarosa', 'Chandler', 'Oso Grande', 'Seascape' and 'Selva', 'Catalina' plant leaves do not display chlorosis, remaining consistent in color intensity throughout the growing season.

One or two bract leaves are present on approximately fifty percent of the leaf stems. As can be seen in FIG. 2, the bract leaves form approximately three-quarters of the way up the leaf stem from the crown to the leaf base. Bract leaves vary in size from less than 1 mm to 23 mm or more. The presence or absence of bract leaves and their size does not appear to be related to the stage of development of the primary leaves or to the size of the plant.

Winged, paired stipules are generally present and shaped similar to other strawberry cultivars. They range in size from about 27 mm to about 42 mm on the fully mature plant, but can be smaller due to poor environmental conditions. The stipules tend to be reddish in color, but the color varies widely in different soil types due to staining.

Tomentum is present on most plants. When present, the hairs are about 1 mm or less in length, sparse and stand perpendicular to the leaf stem in greatest abundance nearest the leaves.

DISEASE AND PEST RESISTANCE

'Catalina' is mildly susceptible to Powdery Mildew (*Sphaerotheca macularis* spp. *fragariae*) and Angular Leaf Spot (*Xanthomonas fragariae*). 'Catalina' is tolerant to Verticillium Wilt (Verticillium Albo-Atrum) and Phytophthora species.

FLOWERING, FRUITING, FRUIT, AND PRODUCTION CHARACTERISTICS

'Catalina' bloom size ranges from between 3 cm and 6 cm, compared with bloom sizes of between 2 cm and 4 cm for 'Chandler' and between 3 cm and 5 cm for 'Camarosa'. 'Catalina' blooms have a large green calyx, the same size or smaller than 'Camarosa' and twice the size of 'Chandler'. 'Catalina' averages between 3 and 6 white petals per bloom, compared with an average of 5.4 petals for 'Chandler' and 6.7 petals for 'Camarosa'. 'Catalina' anthers are double tiered, unlike the single tiered anthers of 'Chandler' and 'Camarosa'.

The fruiting characteristics and fruit quality of 'Catalina' make it very suitable as both a fresh market and processing variety. 'Catalina' grows well in both fumigated and non-fumigated fields and greenhouses throughout all strawberry growing regions of California. 'Catalina' plants vary in runner production depending on the nursery. In general, however, 'Catalina' produces well over 400,000 plants per acre reflecting a 30:1 increase.

'Catalina' produces multicipital inflorescences with several racemes or cymes per peduncle. The inflorescences are very long and erect, initially standing above the plant, and dropping quickly due to the weight of the maturing fruit.

'Catalina' bud initiation takes place in virtually all plants harvested at nursery during the month of October. Increased cold storage after harvest induces runner production and prolongs initiation of buds. 'Catalina' is a medium chilling variety, between 'Chandler' variety which is low chilling and 'Seascape' which is high chilling.

Further, 'Catalina' is a short-day type cultivar producing large amounts of fruit in a relatively short period of time, similar to 'Chandler'. However, 'Catalina' continues to produce fruit well into the summer and displays a pronounced short-day influence in the late summer, similar to 'Selva'.

'Catalina' produces a much higher number of well shaped, unblemished fruit than existing cultivars including 'Camarosa', 'Chandler', 'Oso Grande', 'Selva' and 'Seascape.' It is earlier fruiting and produces larger and more uniform fruit size than 'Camarosa', 'Chandler', 'Seascape' or 'Selva.'

'Catalina' fruit production lacks the substantial peaks and valleys that exist with commonly grown commercial varieties, such as 'Chandler', 'Seascape' and 'Selva'. It also tends to produce fruit in late season without the substantial size reduction characteristic of currently available strawberry cultivars, such as 'Chandler', 'Seascape' and 'Selva'.

'Catalina' is self-fertile, and produces sufficient pollen throughout the season to insure very few malformed fruit. The fruit of 'Catalina' is initially borne on single stems. Separation of primary, secondary, and tertiary fruit takes place in the plant crown. As the season progresses, the separation of the various stages of fruit takes place outside the crown creating a multiple inflorescence.

The mature fruit of 'Catalina' vary in shape from medium- or long-conic, to wide-shouldered, wedge-shaped. The fruit are generally smooth, with the occasional creased or cockscombed primary. 'Catalina' fruit are generally better shaped than the fruit of 'Chandler', 'Oso Grande', 'Camarosa', 'Seascape' and 'Selva', being smoother, more conic and more uniform. It has a waxy cuticle similar to 'Camarosa' and early season 'Chandler' fruit, and greater than 'Selva' fruit and mid to late season 'Seascape' fruit.

'Catalina' fruit vary in size throughout the season, due to environmental and cultural conditions. Advantageously, the fruit loses little size at the various stages of development on the inflorescence. Further, size is retained throughout the growing season with each new inflorescence. Significantly, the size and shape of 'Catalina' fruit does not depend on the amount of fruit borne on each peduncle.

Soluble solid content of 'Catalina' fruit was determined and compared to 'Chandler' fruit throughout an entire growing season utilizing a hand held TY' MUP 11-520-0 ATC Refractometer. Both 'Catalina' fruit and 'Chandler' fruit were consistent in percentage of soluble solids among plants of the same variety, averaging approximately 7.5% soluble solids. There was no statistical difference between 'Catalina' fruit and 'Chandler' fruit at any time during the season.

Internally, 'Catalina' fruit are solid with the occasional primary fruit having a slight cavity. Fruit color is a fine red color, slightly darker than 'Chandler' but not as dark as 'Oso Grande' or 'Seascape'. The exterior color is the same as 'Camarosa'.

'Catalina' fruit flesh displays good color saturation and the interior color substantially matches the exterior color. The achenes range from bright yellow to light red and are positioned even with the skin, which is very firm. Visual comparisons of 'Catalina' fruit color to 'Camarosa' and 'Chandler' leaf color were made according to the PANTONE® Color Formula Guide 1000 (Pantone, Inc. 590 Commerce Boulevard, Carlstadt, NJ USA 07072-3098). The results are given in Table 1 below.

VISUAL COMPARISONS OF 'CATALINA' LEAF AND FRUIT COLOR TO 'CAMAROSA' AND 'CHANDLER' LEAF AND FRUIT COLOR USING THE PANTONE ® COLOR FORMULA GUIDE 1000

| | Adaxial Leaf Color | Abaxial Leaf Color | External Fruit Color | Internal Fruit Color |
|---|---|---|---|---|
| CATALINA | 343C | 348U<br>356U* | 193C | 185C |
| CAMAROSA | 349C | 348U | 193C | 185C |

-continued

VISUAL COMPARISONS OF 'CATALINA' LEAF AND FRUIT COLOR TO 'CAMAROSA' AND 'CHANDLER' LEAF AND FRUIT COLOR USING THE PANTONE ® COLOR FORMULA GUIDE 1000

| | Adaxial Leaf Color | Abaxial Leaf Color | External Fruit Color | Internal Fruit Color |
|---|---|---|---|---|
| CHANDLER | 3435C | 339U | 186C | 179C |

*color ranges between these two specifications

The calyces of 'Catalina' fruit are medium in size and usually clasp the fruit, though a small number of calyces reflex. Some fruit display seeds at the apex but this characteristic does not appear consistently or predictably. 'Catalina' fruit are firm, similar to 'Chandler' and very durable. Further, 'Catalina' fruit have an appealing, very glossy finish.

The flavor of 'Catalina' fruit is excellent, and is comparable to the best flavored cultivars grown in California. Its flavor is similar to 'Chandler' fruit and superior to the 'Seascape' and 'Selva' fruit. Generally, 'Catalina' fruit flavor is sweet with acid levels sufficiently high to impart a slight tang, characteristic of early strawberry varieties.

We claim:

1. The new and distinct variety of strawberry plant described and illustrated and having the characteristics enumerated above.

* * * * *